(12) United States Patent
Redmond et al.

(10) Patent No.: US 11,701,176 B2
(45) Date of Patent: Jul. 18, 2023

(54) SPINAL SURGERY SYSTEM AND METHODS OF USE

(71) Applicant: Warsaw Orthopedic, Inc., Warsaw, IN (US)

(72) Inventors: Jerald Redmond, Germantown, TN (US); Jeffrey Wickham, Ooltewah, TN (US); Pooja Hebbale, San Jose, CA (US); Kelli Armstrong, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 332 days.

(21) Appl. No.: 16/867,800

(22) Filed: May 6, 2020

(65) Prior Publication Data
US 2021/0346092 A1 Nov. 11, 2021

(51) Int. Cl.
| | | |
|---|---|---|
| *A61B 34/10* | (2016.01) | |
| *A61B 90/00* | (2016.01) | |
| *A61B 90/50* | (2016.01) | |
| *A61B 34/20* | (2016.01) | |
| *A61B 34/30* | (2016.01) | |
| *A61B 17/56* | (2006.01) | |

(52) U.S. Cl.
CPC .............. *A61B 34/10* (2016.02); *A61B 34/20* (2016.02); *A61B 34/30* (2016.02); *A61B 2017/564* (2013.01); *A61B 2034/2051* (2016.02); *A61B 2034/2055* (2016.02); *A61B 2090/365* (2016.02); *A61B 2090/3762* (2016.02); *A61B 2090/502* (2016.02)

(58) Field of Classification Search
CPC ......... A61B 34/10; A61B 34/20; A61B 34/30; A61B 2017/564; A61B 2034/2051; A61B 2034/2055; A61B 2090/365; A61B 2090/3762; A61B 2090/502; A61B 2034/105; A61B 2034/107; A61B 2034/2048; A61B 2034/252; A61B 2034/254; A61B 34/25; A61B 2034/101; A61B 2090/364; A61B 2090/366; A61B 2090/372; G02B 2027/014
See application file for complete search history.

(56) References Cited

U.S. PATENT DOCUMENTS

| | | |
|---|---|---|
| 7,774,044 B2 | 8/2010 | Sauer et al. |
| 9,767,608 B2 | 9/2017 | Lee et al. |
| 10,176,642 B2 | 1/2019 | Tran et al. |
| 10,194,990 B2 * | 2/2019 | Amanatullah ......... A61B 34/20 |
| 10,278,777 B1 | 5/2019 | Lang |
| 10,326,975 B2 | 6/2019 | Casas |

(Continued)

*Primary Examiner* — Joel Lamprecht
(74) *Attorney, Agent, or Firm* — Sorell, Lenna & Schmidt, LLP

(57) ABSTRACT

A method for surgically treating a spine comprising the steps of: pre-operatively imaging vertebral tissue; displaying a first image of a surgical treatment configuration for the vertebral tissue from a mixed reality display and/or a second image of a surgical strategy for implementing the surgical treatment configuration with the vertebral tissue from the mixed reality display; determining a surgical plan for implementing the surgical strategy; and intra-operatively displaying a third image of the surgical plan with the vertebral tissue from the mixed reality display. Systems, spinal constructs, implants and surgical instruments are disclosed.

17 Claims, 14 Drawing Sheets

(56) References Cited

U.S. PATENT DOCUMENTS

| | | |
|---|---|---|
| 10,390,887 B2 | 8/2019 | Bischoff et al. |
| 2015/0100091 A1* | 4/2015 | Tohmeh ............. A61B 17/7083 |
| | | 606/279 |
| 2016/0028998 A1* | 1/2016 | Deitz ....................... H04N 7/18 |
| | | 348/77 |
| 2016/0242857 A1* | 8/2016 | Scholl .................... A61B 34/10 |
| 2017/0367771 A1 | 12/2017 | Tako et al. |
| 2018/0262743 A1* | 9/2018 | Casas ................... H04N 13/279 |
| 2019/0167352 A1 | 6/2019 | Mahfouz |
| 2020/0178937 A1* | 6/2020 | Liu ........................... G06T 7/33 |
| 2020/0261156 A1* | 8/2020 | Schmidt ................. G06T 19/20 |

\* cited by examiner

SPINAL SURGERY SYSTEM AND METHODS OF USE

TECHNICAL FIELD

The present disclosure generally relates to medical systems for the treatment of musculoskeletal disorders, and more particularly to a surgical system and method for treating a spine.

BACKGROUND

Spinal disorders such as degenerative disc disease, disc herniation, osteoporosis, spondylolisthesis, stenosis, scoliosis and other curvature abnormalities, kyphosis, tumor and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, interbody devices can be employed with spinal constructs, which include implants such as bone fasteners and vertebral rods to provide stability to a treated region. These implants can redirect stresses away from a damaged or defective region while healing takes place to restore proper alignment and generally support the vertebral members. During surgical treatment, surgical systems including surgical navigation and/or surgical instruments are employed, for example, to facilitate surgical preparation, manipulation of tissue and delivering implants to a surgical site. This disclosure describes an improvement over these prior technologies.

SUMMARY

In one embodiment, a method for surgically treating a spine is provided. The method comprises the steps of: pre-operatively imaging vertebral tissue; displaying a first image of a surgical treatment configuration for the vertebral tissue from a mixed reality display and/or a second image of a surgical strategy for implementing the surgical treatment configuration with the vertebral tissue from the mixed reality display; determining a surgical plan for implementing the surgical strategy; and intra-operatively displaying a third image of the surgical plan with the vertebral tissue from the mixed reality display. In some embodiments, systems, spinal constructs, implants and surgical instruments are disclosed.

In one embodiment, the method comprises the steps of: pre-operatively imaging vertebral tissue; displaying a first image of a segmentation and a surgical reconstruction of the vertebral tissue from a holographic display and/or a second image of a surgical strategy that includes one or more spinal implants with the vertebral tissue from the holographic display; determining a surgical plan for implementing the surgical strategy; and intra-operatively displaying a third image of the surgical plan with the vertebral tissue from the holographic display.

In one embodiment, the method comprises the steps of: pre-operatively imaging vertebral tissue; transmitting data points of the imaging to a computer database and determining a surgical treatment configuration for the vertebral tissue; determining a surgical strategy for implementing the surgical treatment configuration; generating data points representative of a first image of the surgical treatment configuration and a second image of the surgical strategy; displaying the first image and/or the second image from a mixed reality display; determining a surgical plan for implementing the surgical strategy with the vertebral tissue and generating data points representative of a third image of the surgical plan; displaying the third image with the vertebral tissue from the mixed reality display; imaging surgically treated vertebral tissue; generating data points representative of a fourth image comparing the third image and the imaging of the surgically treated vertebral tissue; and displaying the fourth image from the mixed reality display.

BRIEF DESCRIPTION OF THE DRAWINGS

The present disclosure will become more readily apparent from the specific description accompanied by the following drawings, in which.

DETAILED DESCRIPTION

Figure 1:
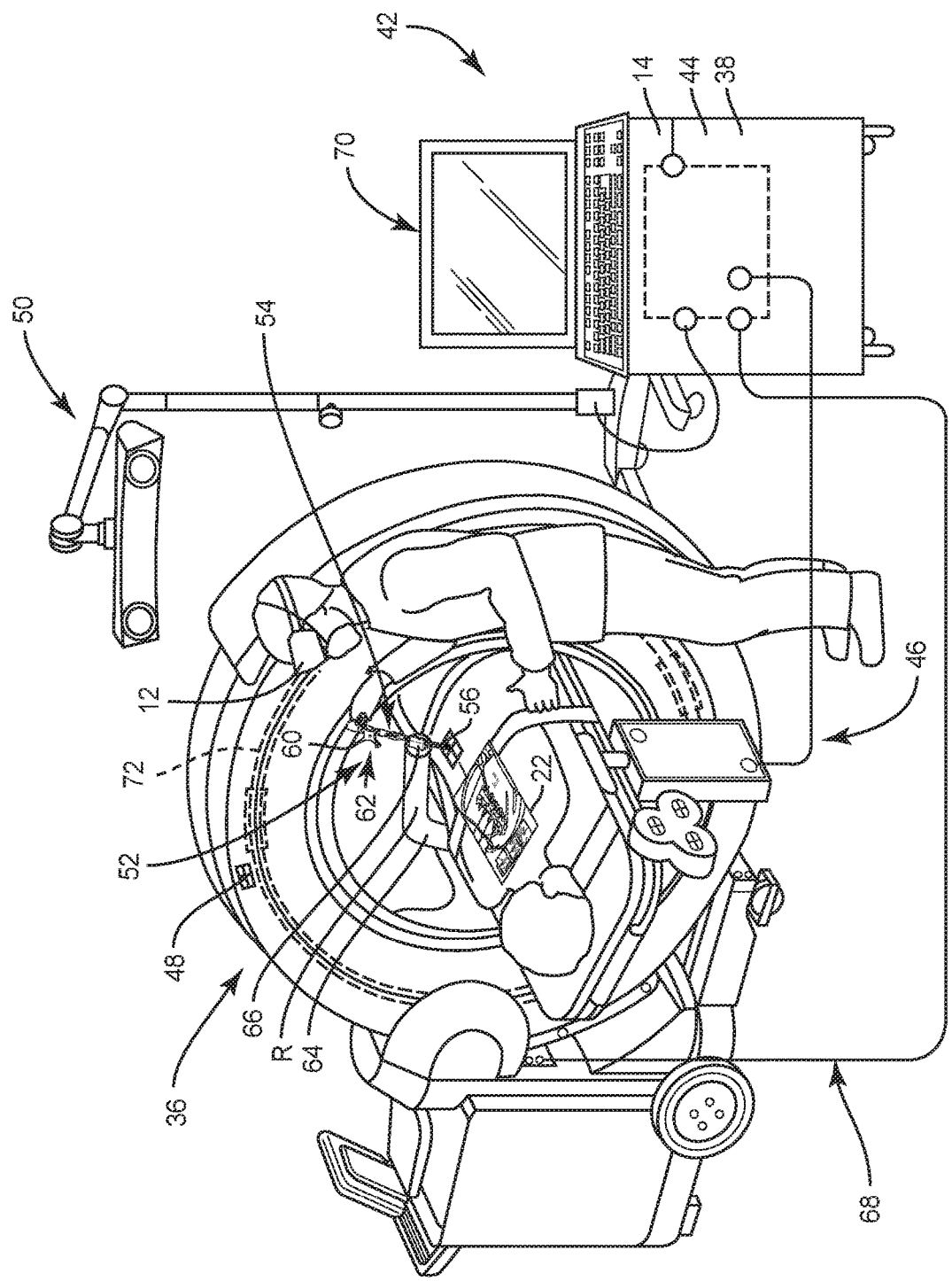
FIG. 1 is a perspective view of components of one embodiment of a surgical system in accordance with the principles of the present disclosure.

The exemplary embodiments of a surgical system are discussed in terms of medical devices for the treatment of musculoskeletal disorders and more particularly, in terms of a surgical system and a method for treating a spine. In some embodiments, the present surgical system includes a mixed reality display or an augmented reality display, and is employed with a method for surgically treating a spine including surgical planning, performing a surgical procedure, intra-operative correction and/or reconciling the performed surgical procedure with the surgical plan. In some embodiments, the present surgical system comprises a display including a holographic display device. In some embodiments, the systems and methods of the present disclosure comprise a mixed reality display or an augmented reality display, surgical robotic guidance, surgical navigation and medical devices including surgical instruments and implants that are employed with a surgical treatment, as described herein, for example, with a cervical, thoracic, lumbar and/or sacral region of a spine.

In some embodiments, the present surgical system includes pre-operative imaging of a patient's vertebrae, for example, through 3D imaging generated from a CT scan. In some embodiments, a computer converts the pre-operative imaging to digital data and transfers the digital data to a mixed reality headset, for example, a holographic headset. In some embodiments, the computer utilizes software to determine segmentation and/or reconstruction of the vertebrae and/or mixed reality/holographic surgical planning that is uploaded to the headset for display from the headset. In some embodiments, the data is transferred to a robotic guidance system and/or surgical navigation system. In some embodiments, the robotic guidance system and/or surgical navigation system includes registered navigation data on actual vertebrae/body coordinates and surgical instruments that are used for the surgical procedure based on emitter arrays that are attached to the surgical instruments and are anchored to a body reference position, for example, a patient's pelvis. In some embodiments, the navigation data is transferred to the headset and/or the computer. In some embodiments, the previously determined surgical plan is holographically overlaid onto the actual patient, including, for example, the patient's vertebrae and/or a surface of the body during the surgical procedure. In some embodiments, intra-operative or post-operative imaging is taken, for example, through 3D imaging generated from a CT scan. In some embodiments, the computer converts the intra-operative or post-operative imaging to digital data and transfers the digital data to the headset for reconciliation of the surgical plan.

In some embodiments, the present surgical system includes a holographic display system that is implemented in an operating room during a surgical procedure such that digital surgical plans are integrated with a patient for procedure execution and reconciliation. In some embodiments, the digital surgical plans are integrated with the patient through a holographic overlay. In some embodiments, the holographic overlay includes a digital surgical plan that is patient specific. In some embodiments, the digital surgical plan utilizes patient specific anatomy data generated from pre-operative images, for example, computed tomography (CT) scans In some embodiments, the holographic overlay is superimposed on a surface of the patient in the operating room during a surgical procedure and implemented as a guide for correction of the surgical procedure.

In some embodiments, the present surgical system includes recognition markers positioned relative to the patient to map the surface of the patient. In some embodiments, a scanner is implemented to map the surface of the patient. In some embodiments, the holographic overlay is implemented in conjunction with a camera and/or sensors to measure physical corrections during the surgical procedure so that the surgical plan can be reconciled.

In some embodiments, the present surgical system and methods include spatially located three dimensional (3D) holograms, for example, holographic overlays for displaying image guidance information. In some embodiments, the present surgical system and methods include cameras, for example, depth sensing cameras. In some embodiments, the depth sensing cameras include infrared, laser, and/or red/green/blue (RGB) cameras. In some embodiments, depth sensing cameras along with simultaneous localization and mapping are employed to digitize the patient, spinal anatomy, and/or the operating room for spatially locating holograms and then displaying the digital information. In some embodiments, the present surgical system and methods include software algorithms, for example, object recognition software algorithms that are implemented for spatially locating the holograms and for displaying digital information. In some embodiments, machine learning algorithms are employed that identify patient anatomical features, instrument features and/or implant features for spatially locating holograms and displaying digital information. In some embodiments, software algorithms are implemented in 3D image processing software employed for the procedure planning including for example, software algorithms for importing, thresholding, masking, segmentation, cropping, clipping, panning, zooming, rotating, measuring and/or registering.

In some embodiments, the present surgical system and methods include depth sensing cameras, for example, infrared, laser, and/or RGB cameras; spatial transducers, for example, electromagnetic, low energy Bluetooth®, and/or inertial measurement units; optical markers, for example, reflective spheres, QR codes/patterns, and/or fiducials; and/or object recognition software algorithms to track a spatial position of a patient, for example, a patient's vertebral bodies and update a digital representation in real time. In some embodiments, the present surgical system and methods include 3D imaging software algorithms implemented to render and display changes in an anatomical position in real-time. In some embodiments, the present surgical system and methods include holographic display technology, for example, optical waveguides to display holograms, image guidance, and/or other digital information in real-time.

In some embodiments, the present surgical system and methods include image guidance and pre-operative software planning tools to define anatomic regions of interest in a patient and danger zones or areas to avoid during surgery for a controlled guidance of tools within defined zones during the procedure. In some embodiments, the present surgical system and methods include depth sensing cameras used simultaneously with localization and mapping to map bone surfaces of a patient during the procedure for use in defining regions of interest and avoidance with image guidance.

In some embodiments, the present surgical system is employed with methods for spinal surgical procedure planning and reconciliation. In some embodiments, the present surgical system is employed with methods including the step of pre-operatively imaging a section of a patient's spine. In some embodiments, the present surgical system is employed with methods including the step of converting the pre-operative imaging into digital data. In some embodiments, the present surgical system is employed with methods including the step of transferring the data to a holographic display system. In some embodiments, the holographic display system includes a processor, a graphics processing unit (GPU), and software for auto-segmentation and planning. In some embodiments, the present surgical system is employed with methods including the step of overlaying the pre-operative data with a holographic surgical plan. In some embodiments, the present surgical system is employed with methods including the step of transferring the holographic surgical plan data to an image guidance or robotic surgical system. In some embodiments, the present surgical system is employed with methods including the step of viewing the holographic overlay superimposed on a patient for procedure execution. In some embodiments, the viewing is performed through a head mounted display for example, goggles or glasses, a tablet, a smartphone, a contact lens and/or an eye loop. In some embodiments, the present surgical system is employed with methods including the step of performing the surgical procedure. In some embodiments, the present surgical system is employed with methods including the step of intra-operatively and/or post-operatively imaging a section of the spine. In some embodiments, the present surgical system is employed with methods including the step of converting the intra-operative and/or post-operative imaging into data. In some embodiments, the present surgical system is employed with methods including the step of transferring the data to the holographic display system. In some embodiments, the present surgical system is employed with methods including the step of comparing the surgical plan with an outcome of the surgical procedure. In some embodiments, the present surgical system is employed with methods including the step of reconciling the surgical outcome with the surgical plan.

In some embodiments, the present surgical system and methods include a surgical plan holographic overlay and/or software that indicates and/or alerts a user, for example, a surgeon, of danger zones located on an anatomy of a patient to assist the surgeon in planning a surgical procedure. In some embodiments, the surgical plan holographic overlay and/or the software generates a warning to the surgeon if a surgical instrument, for example, a drill or a screw is about to enter into a danger zone or a dangerous area. In some embodiments, the present surgical system and methods include a surgical plan holographic overlay and/or software that enables a surgeon to select specific locations, for example, critical bone faces on anatomical areas of a patient such that an alarm or a warning is generated when the specific locations are in danger of being breached. In some embodiments, the surgical system is configured to auto-recognize the specific locations. In some embodiments, the present surgical system and methods include a holographic overlay of an optimized corrected spine that is configured for superimposing over a surface of a patient such that the holographic overlay is implemented as a guide for the surgeon during spinal correction.

In some embodiments, the system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the system of the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues;

as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including mixed and/or augmented reality technology, holographic overlays, surgical navigation, surgical robotic guidance, surgical instruments, spinal constructs, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-11, there are illustrated components of a surgical system 10.

The components of surgical system 10 can be fabricated from biologically acceptable materials suitable for medical applications, including metals, synthetic polymers, ceramics and bone material and/or their composites. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 can be employed, for example, with a minimally invasive procedure, including percutaneous techniques, mini-open and open surgical techniques to manipulate tissue, deliver and introduce instrumentation and/or components of spinal constructs at a surgical site within a body of a patient, for example, a section of a spine. In some embodiments, one or more of the components of surgical system 10 are configured for engagement with one or more components of one or more spinal constructs, which may include spinal implants, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine. In some embodiments, the spinal constructs can be attached with vertebrae in a revision surgery to manipulate tissue and/or correct a spinal disorder, as described herein.

Surgical system 10 is employed in an operating room to assist a surgeon in effectively implementing and executing a surgical procedure. Surgical system 10 utilizes a mixed reality and/or augmented reality display, for example, to holographically overlay digital surgical plans specific to a patient onto a surface of the patient to function as a guide for the surgeon for implementation of the surgical procedure. In some embodiments, surgical system 10 enables the surgeon to reconcile the surgical procedure post-operatively by providing a visual comparison of the end result of the surgical procedure via a holographic overlay that is compared to the digital surgical plan holographic overlay.

Figure 2:
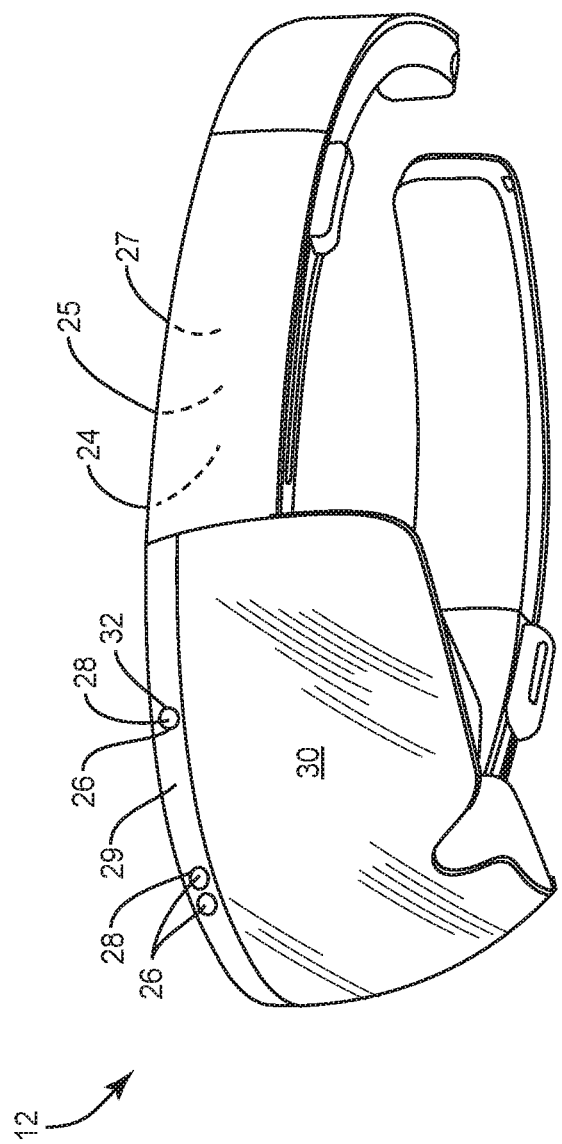
FIG. 2 is a perspective view of components of the surgical system shown in FIG. 1.

Surgical system 10 includes a mixed reality display, for example, a stereoscopic optical see-through headset 12, as shown in FIG. 2. Headset 12 is configured to communicate with a database 14 loaded on a computer 42 that transmits data points of pre-operative imaging 16 of a selected portion of a patient's anatomy, for example, vertebral tissue to headset 12 such that pre-operative imaging 16 can be outputted from headset 12. Computer 42 utilizes the data points of pre-operative imaging 16 to generate images of surgical treatments, surgical strategies and surgical plans to be displayed on headset 12. Headset 12 is configured to display a surgical treatment configuration image 18 for the vertebral tissue, a surgical strategy image 20 for implementing the surgical treatment with the vertebral tissue and intra-operatively displaying a surgical plan image 22 for implementing the surgical plan with the vertebral tissue in a common coordinate system. See, for example, the embodiments and disclosure of systems and methods of components of a headset, shown and described in commonly owned and assigned U.S. patent application Ser. No. 16/867,812 filed May 6, 2020, and published as U.S. patent application Publication No. US20210346093, on Nov. 11, 2021, the entire contents of which being incorporated herein by reference.

Figure 6:
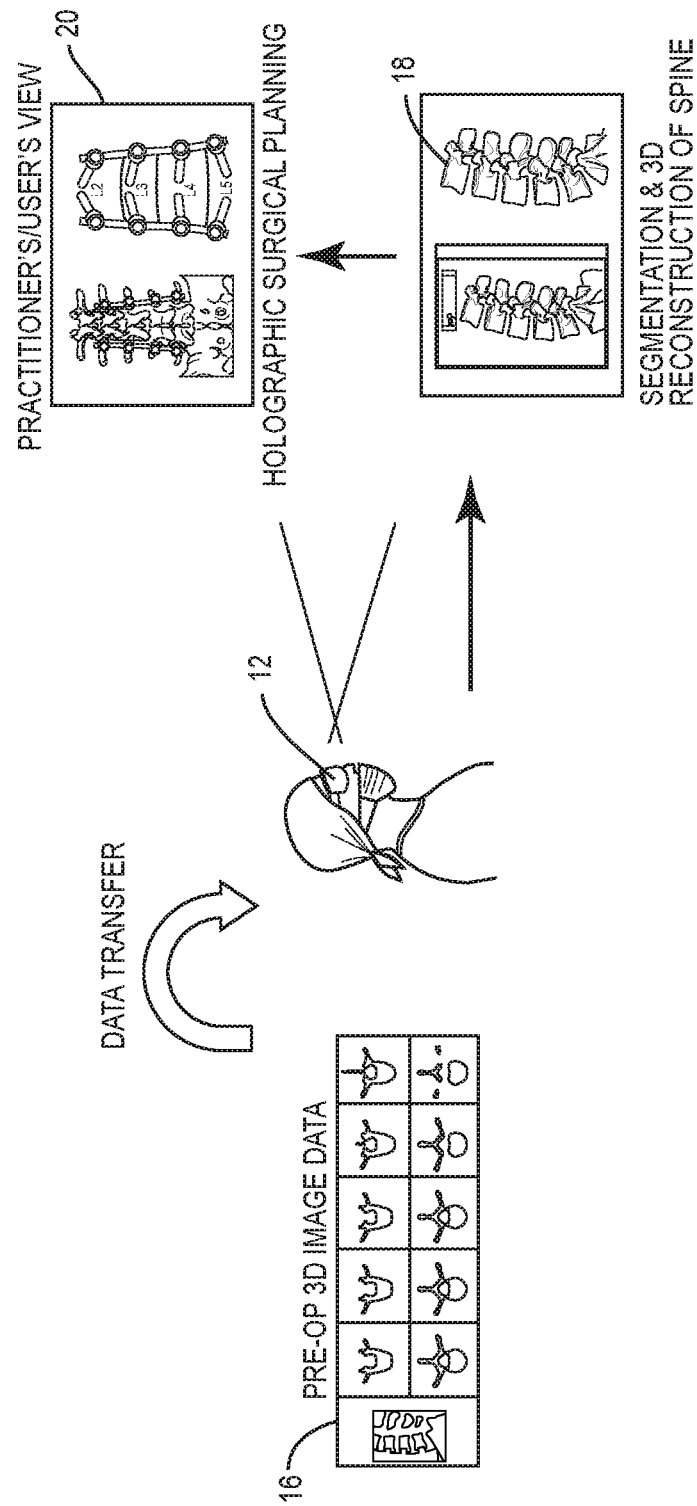
FIG. 6 is a schematic diagram illustrating components of one embodiment of a surgical system including a representation of imaging and steps of a method in accordance with the principles of the present disclosure.
Figure 8:
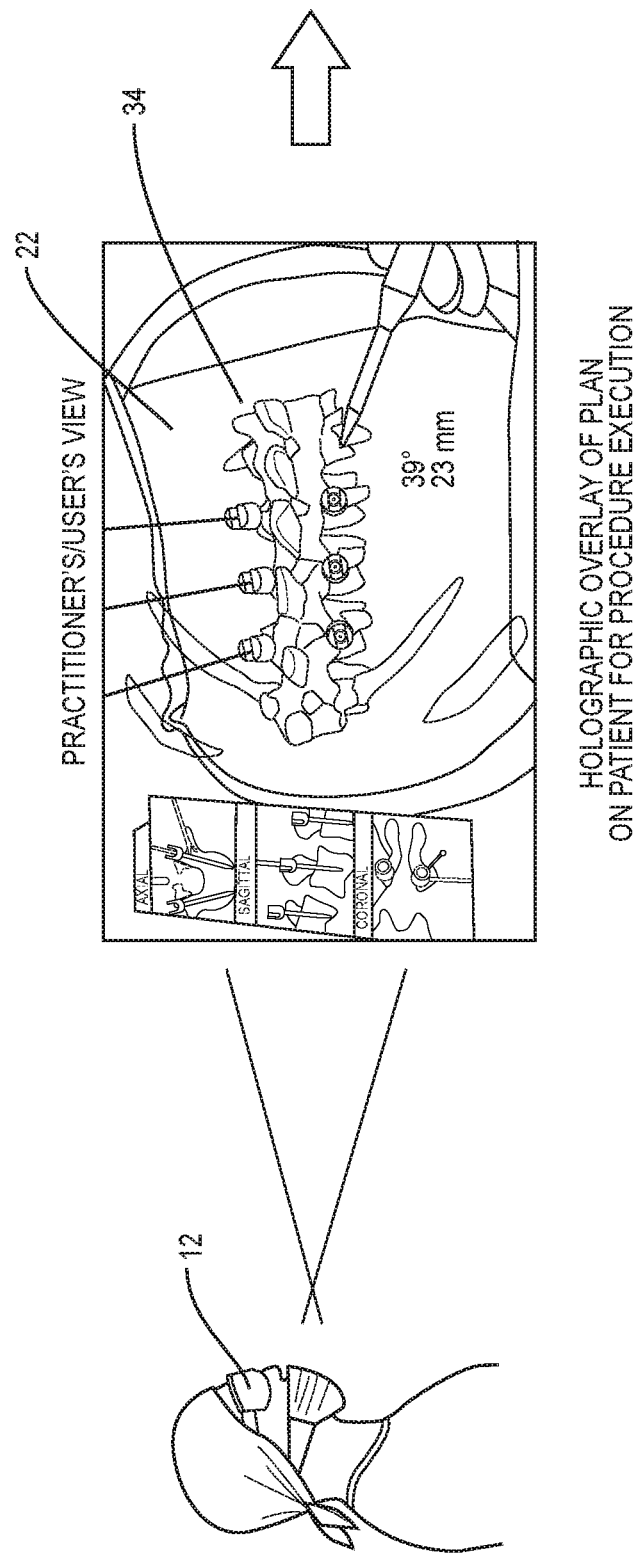
FIG. 8 is a schematic diagram illustrating components of one embodiment of a surgical system including a representation of imaging and steps of a method in accordance with the principles of the present disclosure.
Figure 9:
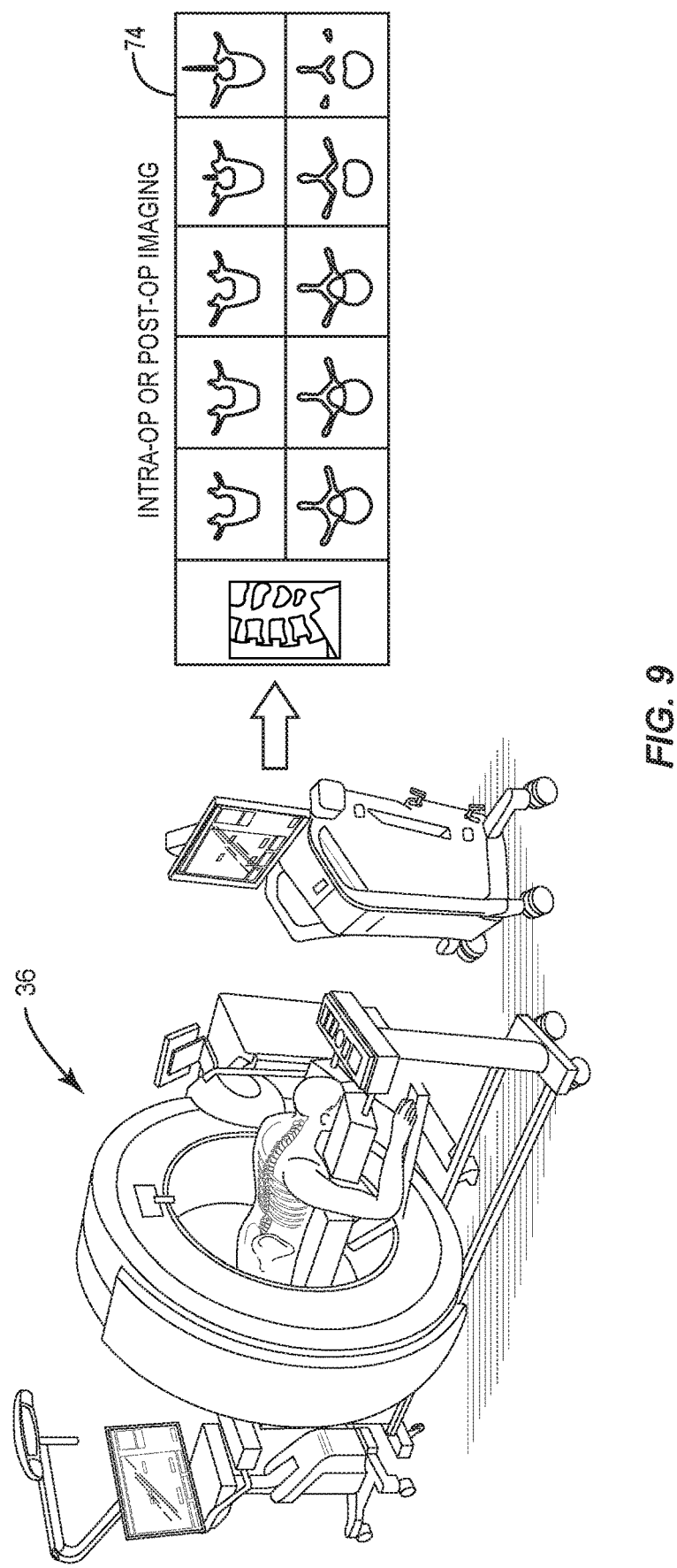
FIG. 9 is a perspective view of components of one embodiment of a surgical system including a representation of imaging of vertebrae in accordance with the principles of the present disclosure.
Figure 10:
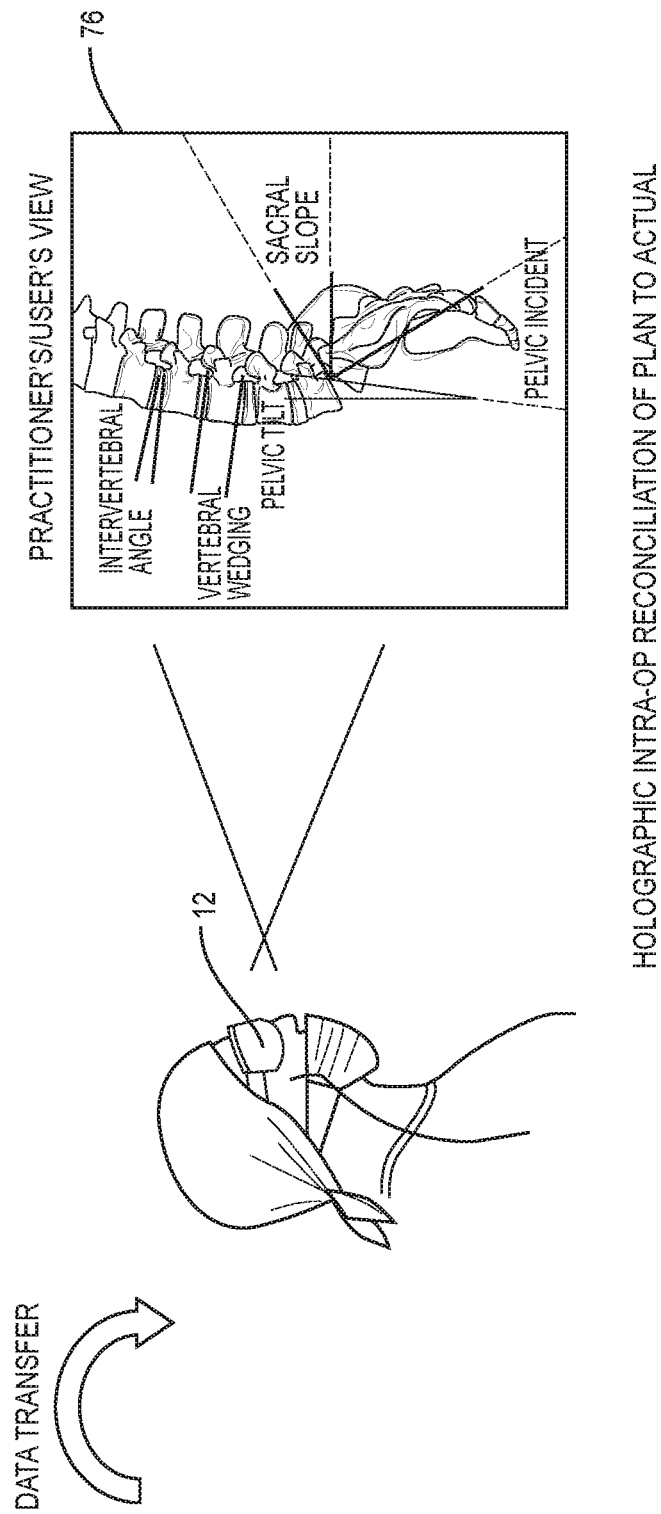
FIG. 10 is a schematic diagram illustrating components of one embodiment of a surgical system including a representation of imaging and steps of a method in accordance with the principles of the present disclosure.
Figure 11:
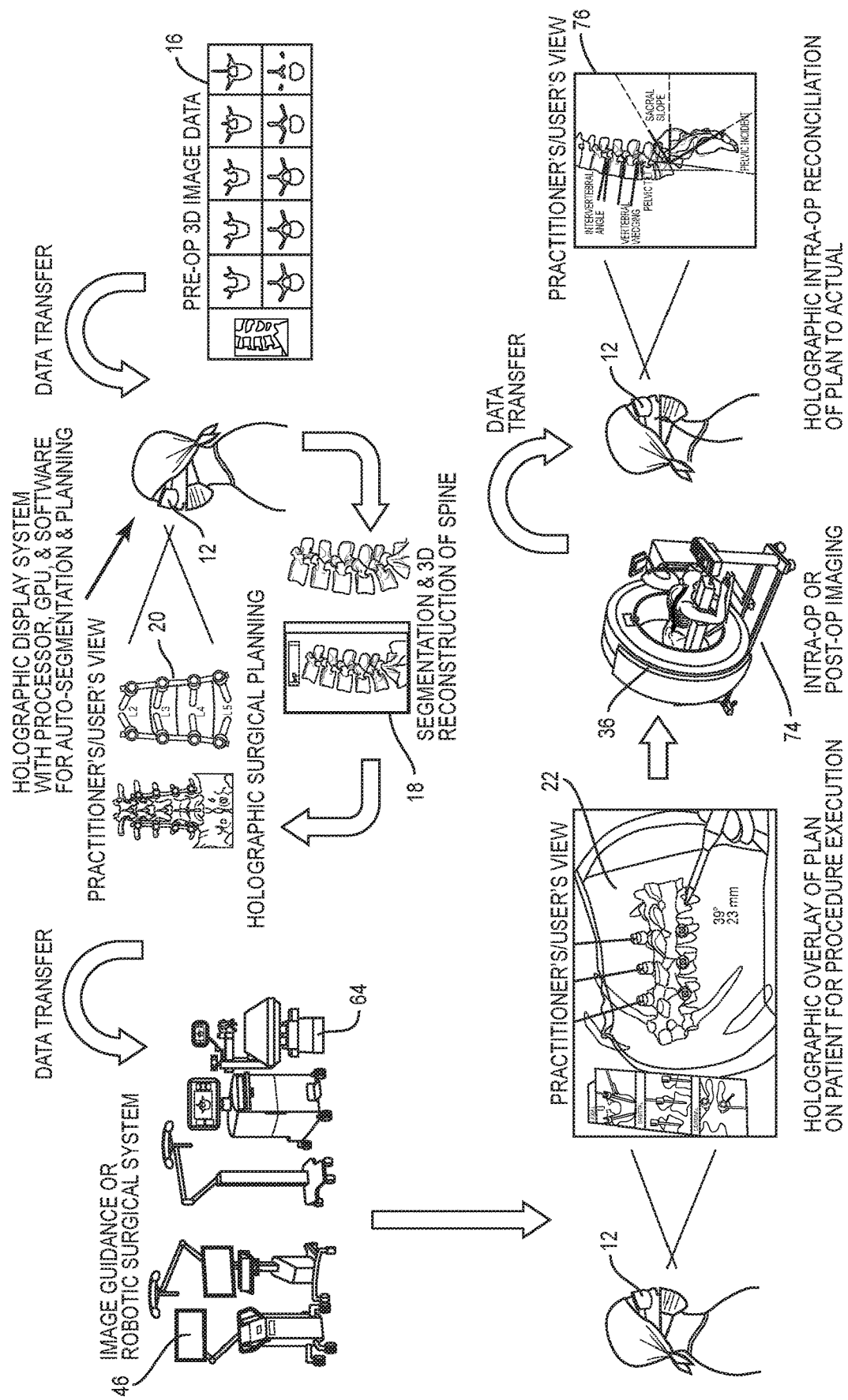
FIG. 11 is a schematic diagram illustrating components of one embodiment of a surgical system including a representation of imaging and steps of a method in accordance with the principles of the present disclosure.

Surgical treatment image 18 includes a segmentation of the vertebral tissue and/or a surgical reconstruction of the vertebral tissue, as shown in FIG. 6. Surgical strategy image 20 includes a holographic overlay of the patient's spine rendered from pre-operative imaging 16, as shown in FIG. 6. In some embodiments surgical strategy image 20 includes a holographic overlay of one or more spinal implants on a surgical reconstruction of the vertebral tissue. Surgical plan image 22 includes a holographic overlay having indicia on the vertebral tissue, as shown in FIG. 8. The indicia represents one or more anatomical zones on the vertebral tissue.

Headset 12 includes a processor 24, for example, a central processing unit (CPU). Processor 24 is configured to execute one or more instructions, for example, software instructions in operation of headset 12, as described herein. Processor 24 functions as the primary coordinating component of headset 12 and is configured to access programs, data, and/or other functions from random access memory (RAM) when called by an operating system (OS) of headset 12. Processor 24 interprets instructions that are related to ordered tasks before sending it back to the RAM for execution via a bus of headset 12 in the correct order of execution.

Headset 12 includes a rendering processor, for example, a graphics processor 25. Graphics processor 25 includes a graphics processing unit (GPU). Graphics processor 25 is configured to render images, animations and/or video for display on headset 12. In some embodiments, processor 24 instructs graphics processor 25 to render the images, animations and/or video. Images rendered include, for example, surgical treatment configuration image 18, surgical strategy image 20 and/or surgical plan image 22. Graphics processor 25 is configured to communicate with a camera 26 of headset 12 which captures a digital video image of the real world and transfers the digital video image to graphics processor 25 in real-time. Graphics processor 25 combines the video image feed with computer-generated images (e.g., virtual content), for example, surgical treatment configuration image 18, surgical strategy image 20 and/or surgical plan image 22 and displays the images on headset 12. In some embodiments, headset 12 alternatively or in addition to graphics processor 25 includes a holographic processor 27. Holographic processor 27, for example a holographic processing unit (HPU) is configured to conduct the processing that integrates digital video image data of the real world, data for augmented reality and/or user input (see, for example, the holographic processing unit sold by Microsoft Corporation, having a place of business in Redmond, Wash., USA).

Headset 12 includes camera 26, for example, a stereoscopic camera, for example, a pair of cameras. Camera 26 is disposed on a front side 29 of headset 12, as shown in FIG. 2. Camera 26 is configured to capture real-time digital stereoscopic video images of the patient, for example, the vertebral tissue and/or real-time images of an external environment of the real world, for example, the operating room during the surgical procedure. The real-time images captured by camera 26 are outputted to headset 12 and displayed on a lens 30 of headset 12. The real-time images captured by camera 26 and the surgical plan image 22 rendered from graphics processor 25 are displayed concurrently and intra-operatively. In some embodiments, camera 26 includes a depth sensing camera and/or an environment camera. In some embodiments, the depth sensing camera can work in tandem with the environment camera. In some embodiments, the depth sensing camera includes infrared, laser, and/or RGB cameras.

Headset 12 includes a sensor 28. Sensor 28 is disposed on front side 29 of headset 12. Sensor 28 includes a 3D scanner 32 configured to determine and capture a 3D surface image 34, for example, the vertebral tissue of the patient, as shown in FIG. 8 so that, for example, surgical plan image 22 and/or other images can be holographically overlaid onto the patient through headset 12. In some embodiments, camera 26 along with simultaneous localization and mapping implemented by 3D scanner 32 digitizes the patient, spinal anatomy, and/or the operating room for spatially locating holograms and then displays the digital information via lens 30 of headset 12. Digital video (e.g., stereoscopic video) combined with 3D surface image 34 determined by 3D scanner 32 and pre-operative imaging 16 is combined by graphics processor 25 for display.

In some embodiments, 3D scanner 32 implements simultaneous localization and mapping (SLAM) technology to determine 3D surface image 34. SLAM technology simultaneously localizes (finds the location of an object/sensor with reference to its surroundings) and maps the layout and framework of the environment for headset 12. This can be done using a range of algorithms that simultaneously localize and map the objects.

In some embodiments, 3D surface image 34 of the vertebral tissue can be determined through the use of 3D scanner 32, camera 26 and recognition markers (not shown) positioned relative to the patient and/or on a surface of the patient to map the surface of the patient. In some embodiments, the recognition markers may be attached to the patient to provide anatomic landmarks of the patient during the 3D scanning process. The recognition markers, alone or in combination with other tracking devices, such as inertial measurement units (IMU), may be attached to 3D scanner 32, camera 26, and/or the surgeon (e.g. through headset 12).

In some embodiments, 3D surface image 34 of the vertebral tissue can be determined through the use of 3D scanner 32, camera 26, and/or for example, spatial transducers, for example, electromagnetic, low energy Bluetooth®, and/or inertial measurement units; optical markers, for example, reflective spheres, QR codes/patterns, and/or fiducials; and/or object recognition software algorithms to track a spatial position of a patient, for example, a patient's vertebral tissue, for example, vertebral bodies and update a digital representation in real time.

In some embodiments, headset 12 includes sensor 28, motion sensors, acoustic/audio sensors (where the audio is transmitted to speakers (not shown) on headset 12), laser rangefinders, and/or visual sensors. In some embodiments, headset 12 includes sensor 28 and additional sensors including accelerometers, magnetometers, and/or gyroscopes which measure motion and direction in space of headset 12 and enables translational movement of headset 12 in an augmented environment.

3D surface image 34 is registered via processor 24 functioning as a registration processor. In some embodiments, processor 24 registers 3D surface image 34 and a graphical representation of pre-operative imaging 16. In some embodiments, the registered images can be uploaded to a computer 42, as described herein, external to headset 12. The registered 3D surface image 34 will be automatically blended with the registered graphical representation of pre-operative imaging 16. The registered images can be displayed on headset 12 and/or can be projected over the patient as a holographic overlay.

Lens 30 includes a screen that employs holographic display technology, for example, optical waveguides to display holograms, image guidance, and/or other digital information in real-time. In some embodiments, headset 12 via lens 30 displays a 360° view through the patient of pre-operative imaging 16, surgical treatment configuration image 18, surgical strategy 20 image and/or surgical plan image 22. In some embodiments, headset 12 includes, for example, goggles or glasses (see, for example, similar goggles or glasses of HoloLens® or HoloLens® 2 (Microsoft Corporation, Redmond, Wash., USA); or Magic Leap® (Magic Leap, Inc, Florida, USA) and/or DreamGlass® (Dreamworld, California, USA)).

In some embodiments, headset 12 employs holographic display technology where light particles (e.g., photons) bounce around in a light engine within the device. The light particles enter through two lenses 30 of the headset 12 where the light particles ricochet between layers of blue, green and red glass before reaching the back of the surgeon's eyes. Holographic images form when the light is at a specific angle. In some embodiments, headset 12 includes a contact lens and/or an eye loop. In some embodiments, headset 12 includes a handheld device including, for example, a tablet or a smartphone. In some embodiments, system 10 includes projector technology including a display plate as an alternative to headset 12 or in addition to headset 12.

As described herein, database 14 transmits data points of pre-operative imaging 16, surgical treatment configuration image 18, surgical strategy 20 image and/or surgical plan image 22 to headset 12 for display. In some embodiments, database 14 transmits data points of pre-operative imaging 16 to headset 12 so that headset 12 can generate surgical treatment configuration image 18, surgical strategy 20 image and surgical plan image 22. In some embodiments, the data points of pre-operative imaging 16 can be transmitted wirelessly or uploaded into headset 12.

Figure 3:
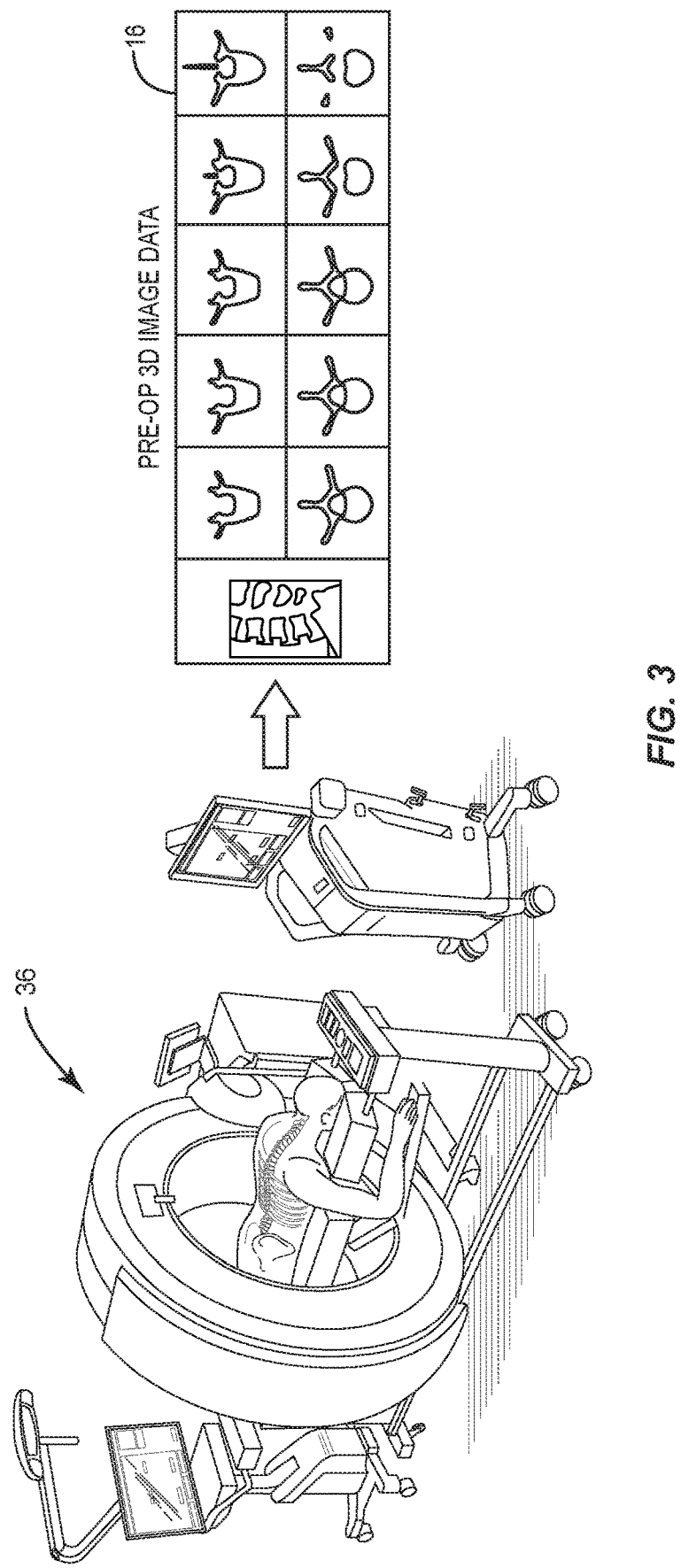
FIG. 3 is a perspective view of components of one embodiment of a surgical system including a representation of imaging of vertebrae in accordance with the principles of the present disclosure.

Pre-operative imaging 16 is generated by an imaging device 36, as shown in FIG. 3. Imaging device 36 is configured to generate pre-operative, intra-operative and/or post-operative images of a selected portion of the patient's anatomy, for example, the vertebral tissue. In some embodiments, imaging device 36 is configured to generate two dimensional (2D) and/or three dimensional (3D) images. In some embodiments, imaging device 36 includes, for example, a CT scan. In some embodiments, imaging device 36 includes an MR scan, ultrasound, positron emission tomography (PET), and/or C-arm cone-beam computed tomography. Pre-operative imaging 16 is then converted into image data to store within database 14. In some embodiments, pre-operative imaging 16 is converted into image data by a software program.

Database 14 is stored on a tangible storage device 38 that includes computer-readable instructions. In some embodiments, storage device 38 includes a hard drive of computer 42. In some embodiments, storage device 38 is an external hard drive unit. In some embodiments, storage device 38 includes a magnetic storage device, for example, a floppy diskette, magnetic strip, SuperDisk, tape cassette, or zip diskette; an optical storage device, for example, a Blu-ray disc, CD-ROM disc, CD-ft CD-RW disc, DVD-R, DVD+R, DVD-RW, or DVD+RW disc; and/or flash memory devices, for example, USB flash drive, jump drive, or thumb drive, CompactFlash (CF), M.2, memory card, MMC, NVMe, SDHC Card, SmartMedia Card, Sony Memory Stick, SD card, SSD or xD-Picture Card. In some embodiments, storage device 38 includes online storage, cloud storage, and/or network media storage. In some embodiments, headset 12 can access database 14/storage device 38 wirelessly. In some embodiments, specific data from database 14 can be uploaded to headset 12, such as intraoperative imaging 16 data, for display.

Figure 4:
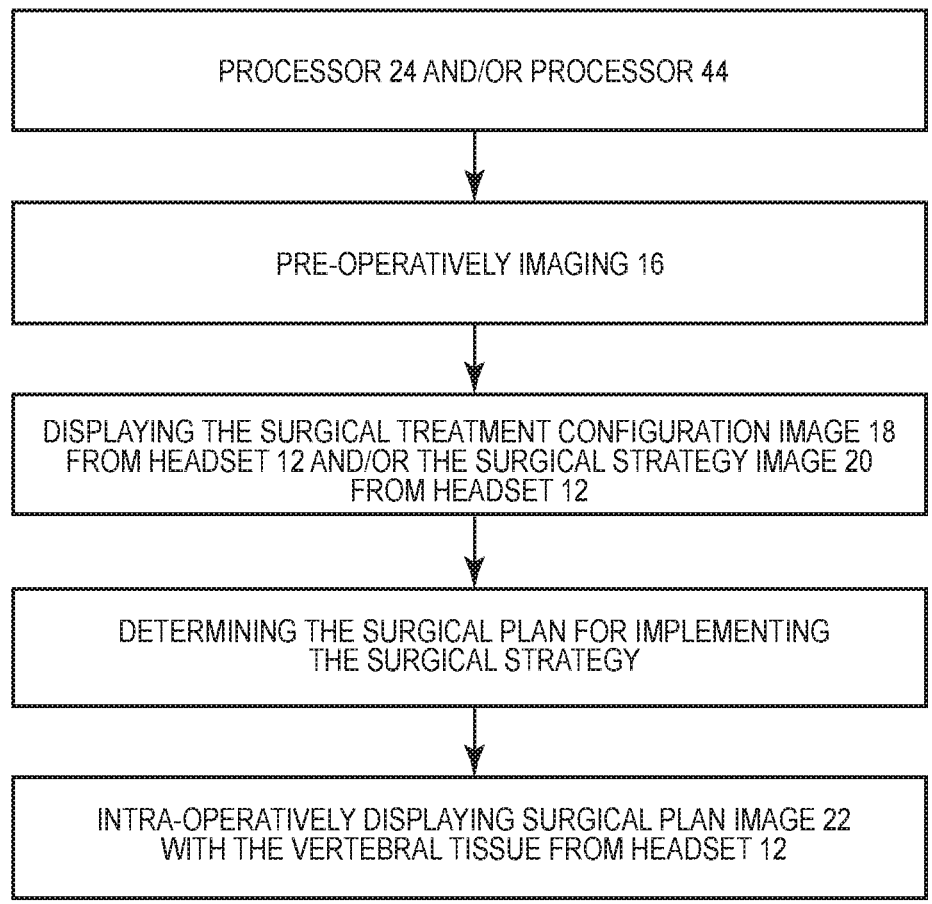
FIG. 4 is a flow diagram illustrating representative steps of one or more embodiments of a method and a surgical system in accordance with the principles of the present disclosure.

As shown in FIG. 4, processor 24 and/or a processor 44, for example, a CPU of computer 42 execute the instructions in operation of system 10. Processor 24 and/or processor 44 execute instructions for pre-operatively imaging 16, displaying surgical treatment configuration image 18 for the vertebral tissue from headset 12 and/or surgical strategy image 20 for implementing the surgical treatment configuration with the vertebral tissue from headset 12, determining the surgical plan for implementing the surgical strategy, and intra-operatively displaying surgical plan image 22 with the vertebral tissue from headset 12.

Computer 42 generates surgical treatment image 18, surgical strategy image 20 and surgical plan image 22, as shown in FIGS. 6 and 8 via a software program. In some embodiments, the software program includes, for example, Mazor X™, Mazor X™ Align, and/or Stealthstation™ sold by Medtronic Navigation, Inc. having a place of business in Louisville, Colo. In some embodiments, the software program is 3D image processing software that includes software algorithms employed for the procedure planning including for example, software algorithms for importing, thresholding, masking, segmentation, cropping, clipping, panning, zooming, rotating, measuring and/or registering. The software program is preloaded onto computer 42, the surgical strategies and plans are generated by the software program, the surgical strategies and plans are uploaded onto headset 12 and graphics processor 25 renders the images so that the images are outputted from lens 30 for display. In some embodiments, the software program is alternatively pre-loaded onto headset 12, the strategies and plans are generated from the software and headset 12 displays the strategies and plans from lens 30.

In some embodiments, headset 12 implements software algorithms, for example, object recognition software algorithms for spatially locating holograms and displaying the digital information, for example, the holographic overlays. In some embodiments, machine learning algorithms are employed that identify patient anatomical features, instrument features and/or implant features for spatially locating holograms and displaying digital information.

In some embodiments, headset 12 implements software and/or surgical plan image 22 indicates and/or alerts the surgeon, of danger zones located on an anatomy, for example, the vertebral tissue of the patient to assist the surgeon in planning the surgical procedure. In some embodiments, danger zones include, spinal nerves, for example, C1 to C8, T1-T12, L1-L5, S1 to S5 and/or the coccyxgeal nerve. In some embodiments, a danger zone includes the posterior triangle of the neck, including the great auricular, lesser occipital, spinal accessory, supraclavicular, phrenic, and suprascapular nerves. In some embodiments, danger zones include areas to avoid so that the likelihood of a dura tear is reduced including the caudal margin of the cranial lamina, cranial margin of the caudal lamina, herniated disc level, and medial aspect of the facet joint adjacent to the insertion of the hypertrophic ligamentum flavum. In some embodiments, surgical plan image 22 and/or the software generates a warning to the surgeon if a surgical instrument, for example, a drill or a screw is about to enter into a danger zone or a dangerous area. In some embodiments, the alerts, alarms and/or warnings include human readable visual indicia, for example, a label, color coding, numbers or an icon, human readable tactile indicia, for example, raised portions, dimples and/or texturing, and/or human detectable audible indicia.

In some embodiments, headset 12 implements software and/or surgical plan image 22 enables a surgeon to select specific locations, for example, critical bone faces on anatomical areas of the patient such that an alarm or a warning is generated when the specific locations are in danger of being breached. In some embodiments, headset 12 is configured to auto-recognize the specific locations.

Figure 7:
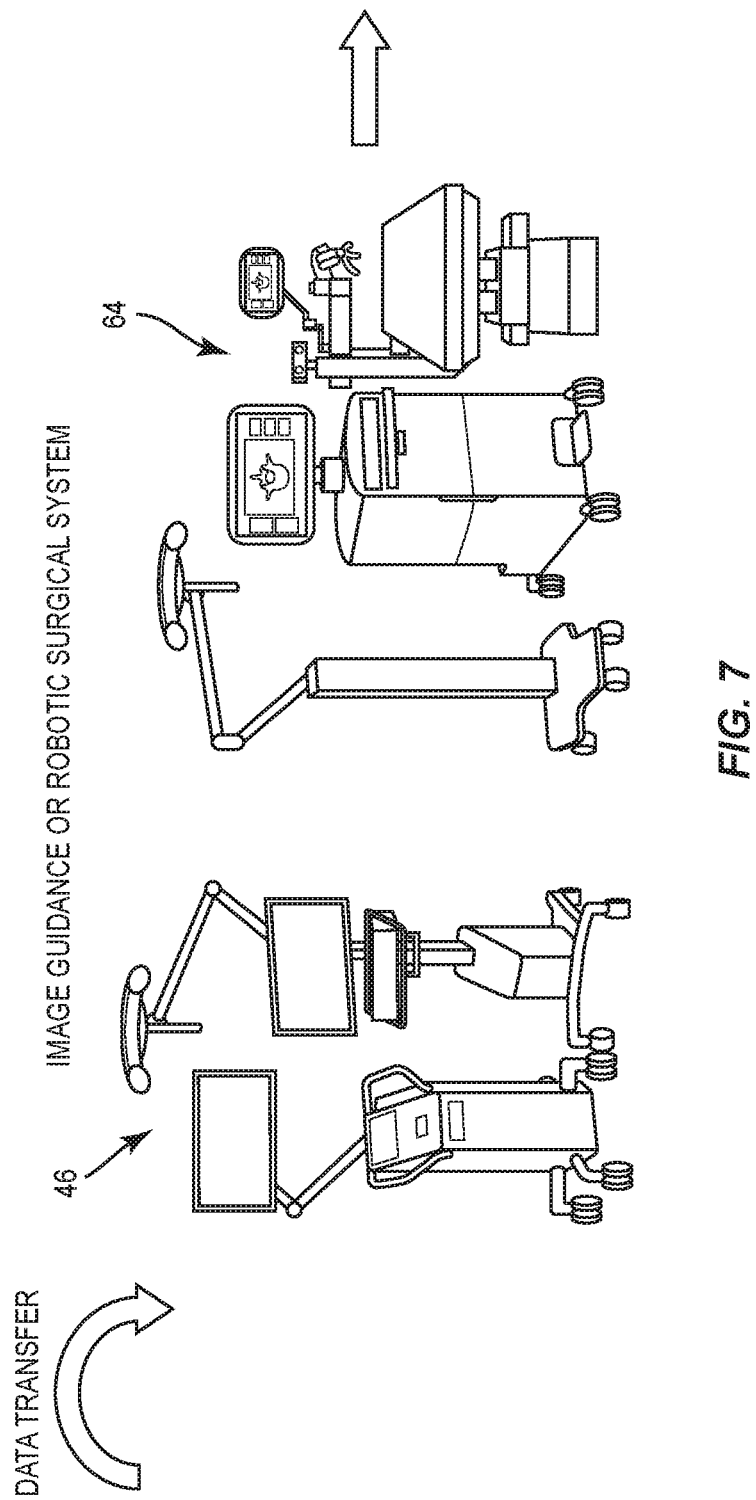
FIG. 7 is a schematic diagram illustrating components of one embodiment of a surgical system and representative steps of embodiments of a method in accordance with the principles of the present disclosure.

An image guidance system 46 is provided, as shown in FIGS. 1 and 7. Headset 12 and/or computer 42 is configured to transfer data, for example, preoperative imaging 16, surgical treatment image 18, surgical strategy image 20 and/or surgical plan image 22 to image guidance system 46. Image guidance system 46 includes a tracking device 48 having a sensor, for example a sensor array 50 that communicates a signal representative of a position of an image guide 52 connected with a surgical instrument 54 or a spinal implant 56 relative to the vertebral tissue. In some embodiments, one or more image guides 52 can be implemented. In some embodiments, one or more surgical instruments 54 and/or one or more spinal implants 56 can include image guide 52 and be implemented in image guidance system 46. In some embodiments, surgical instrument 54 may include, for example, a driver, extender, reducer, spreader, blade, forcep, elevator, drill, cutter, cannula, osteotome, inserter, compressor and/or distractor.

Tracking device 48 is configured to track a location and orientation of headset 12 in the common coordinate system.

Tracking device 48 is configured to communicate with a processor of image guidance system 46 to generate a storable image of surgical instrument 54 and/or spinal implant 56 relative to the vertebral tissue for display from headset 12, as shown in FIG. 1. In some embodiments, the processor is processor 44 of computer 42. The storable images of surgical instrument 54 and/or spinal implant 56 can be selected intra-operatively and displayed on headset 12 with surgical plan 22.

In some embodiments, image guide 52 includes for example, fiducials 60. In some embodiments, fiducials 60 include at least one light emitting diode. In some embodiments, image guide 52 may include other devices capable of being tracked by sensor array 50, for example, a device that actively generates acoustic signals, magnetic signals, electromagnetic signals, radiologic signals. In some embodiments, image guide 52 includes human readable visual indicia, human readable tactile indicia, human readable audible indicia, one or more components having markers for identification under x-ray, fluoroscopy, CT or other imaging techniques, a wireless component, a wired component, and/or a near field communication component. In some embodiments, image guide 52 may be removably attached to a navigation component/instrument tracking device, for example, an emitter array 62 attached to surgical instrument 54 and/or spinal implant 56, as shown in FIG. 1. In some embodiments, one or more image guides 52 each include a single ball-shaped marker.

Image guidance system 46 is connected with a robotic guidance system 64 having a surgical guide, for example an end effector 66 connected to a robotic arm R, as shown in FIGS. 1 and 7. Data from image guidance system 46 and robotic guidance system 64 is configured for transmission to headset 12. During the surgical procedure, headset 12 is configured to display surgical plan image 22 on the surface of the patient while camera 26 of headset 12 provides real-time images of the patient, as shown in FIGS. 1 and 8. During the surgical procedure, headset 12 displays the storable image of surgical instrument 54 and/or spinal implant 56 and robotic guidance system 64 will assist the surgeon in executing the procedure by operating, delivering and/or introducing surgical instrument 54 and/or spinal implant 56.

Surgical robotic guidance system 64 is employed with surgical instrument 54 and/or spinal implant 56 for manipulating vertebral tissue, and for delivering and introducing spinal implant 56 for engagement with the vertebral tissue. Robotic arm R includes position sensors (not shown), which measure, sample, capture and/or identify positional data points of end effector 66 in three dimensional space for a guide-wireless insertion of spinal implant 56 with the vertebral tissue. In some embodiments, the position sensors of robotic arm R are employed in connection with a surgical navigation system 68, as shown in FIG. 1, to measure, sample, capture and/or identify positional data points of end effector 66 in connection with the surgical procedure, as described herein. The position sensors are mounted with robotic arm R and calibrated to measure positional data points of end effector 66 in three dimensional space, which are communicated to computer 42.

Surgical instrument 54 is configured for disposal adjacent a surgical site such that navigation component, for example, emitter array 62 is oriented relative to sensor array 50 to facilitate communication between emitter array 62 and sensor array 50 during the surgical procedure, as described herein. Emitter array 62 is configured to generate a signal representative of a position of spinal implant 56 relative to surgical instrument 54 and/or vertebral tissue. In some embodiments, emitter array 62 is connected with surgical instrument 54 via an integral connection, friction fit, pressure fit, interlocking engagement, mating engagement, dovetail connection, clips, barbs, tongue in groove, threaded, magnetic, key/keyslot and/or drill chuck.

Emitter array 62 is configured for generating a signal to sensor array 50 of surgical navigation system 68, as shown in FIG. 1 and described herein. In some embodiments, the signal generated by emitter array 62 represents a position of spinal implant 56 relative to surgical instrument 54 and relative to vertebral tissue. In some embodiments, the signal generated by emitter array 62 represents a three dimensional position of spinal implant 56 relative to the vertebral tissue.

In some embodiments, sensor array 50 receives signals from emitter array 62 to provide a three-dimensional spatial position and/or a trajectory of spinal implant 56 relative to surgical instrument 54 and/or the vertebral tissue. Emitter array 62 communicates with 44 processor of computer 42 of surgical navigation system 68 to generate data for display of an image on a monitor 70, as described herein. In some embodiments, sensor array 50 receives signals from emitter array 62 to provide a visual representation of a position of spinal implant 56 relative to surgical instrument 54 and/or the vertebral tissue. See, for example, similar surgical navigation components and their use as described in U.S. Pat. Nos. 6,021,343, 6,725,080, 6,796,988, the entire contents of each of these references being incorporated by reference herein.

Surgical navigation system 68 is configured for acquiring and displaying medical imaging, for example, pre-operative image 16 and/or surgical plan image 22 appropriate for a given surgical procedure. In some embodiments, pre-operative image 16 of a patient is collected, as described above. In some embodiments, surgical navigation system 68 can include imaging device 36, as described above. In some embodiments, imaging device 36 is an O-arm® imaging device sold by Medtronic Navigation, Inc. having a place of business in Louisville, Colo., USA. Imaging device 36 may have a generally annular gantry housing that encloses an image capturing portion 72.

In some embodiments, image capturing portion 72 may include an x-ray source or emission portion and an x-ray receiving or image receiving portion located generally or as practically possible 180 degrees from each other and mounted on a rotor (not shown) relative to a track of image capturing portion 72. Image capturing portion 72 can be operable to rotate 360 degrees during image acquisition. Image capturing portion 72 may rotate around a central point or axis, allowing image data of the patient to be acquired from multiple directions or in multiple planes. Surgical navigation system 68 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 68 can include C-arm fluoroscopic imaging systems, which can generate three-dimensional views of a patient. The position of image capturing portion 72 can be precisely known relative to any other portion of an imaging device of navigation system 68. In some embodiments, a precise knowledge of the position of image capturing portion 72 can be used in conjunction with image guidance system 46 to determine the position of image capturing portion 72 and the image data relative to the patient.

Image guidance system 46 can include various portions that are associated or included with surgical navigation system 68. In some embodiments, image guidance system 46 can also include a plurality of types of tracking systems, for example, an optical tracking system that includes an optical localizer, for example, sensor array 50 and/or an EM tracking system that can include an EM localizer. Various tracking devices can be tracked with image guidance system 46 and the information can be used by surgical navigation system 68 to allow for a display of a position of an item, for example, a patient tracking device, tracking device 48, and an instrument tracking device, for example, emitter array 62, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

In some embodiments, surgical navigation system 68 provides for real-time tracking of the position of spinal implant 56 relative to surgical instrument 54 and/or tissue for example, the vertebral tissue can be tracked. Sensor array 50 is located in such a manner to provide a clear line of sight with emitter array 62, as described herein. In some embodiments, fiducial markers 60 of emitter array 62 communicate with sensor array 50 via infrared technology. Sensor array 50 is coupled to computer 42, which may be programmed with software modules that analyze signals transmitted by sensor array 50 to determine the position of each object in a detector space.

As described above, system 10 allows a practitioner the ability to reconcile the surgical procedure post-operatively. After the surgical procedure has been completed, intra-operative image 74 or post-operative image of surgically treated vertebral tissue is generated by imaging device 36. Intra-operative image 74 is converted into image data to store within database 14. Computer 42 generates an image 76 that compares surgical plan image 22 and intra-operative image 74 of the surgically treated vertebral tissue via the software program described above. Image 76 includes a holographic reconciliation overlay of the surgical plan to the surgically treated vertebral tissue. Image 76 is uploaded to headset 12 for display so that the outcome of the surgical procedure can be compared to the surgical plan and reconciled if required.

Figure 5:
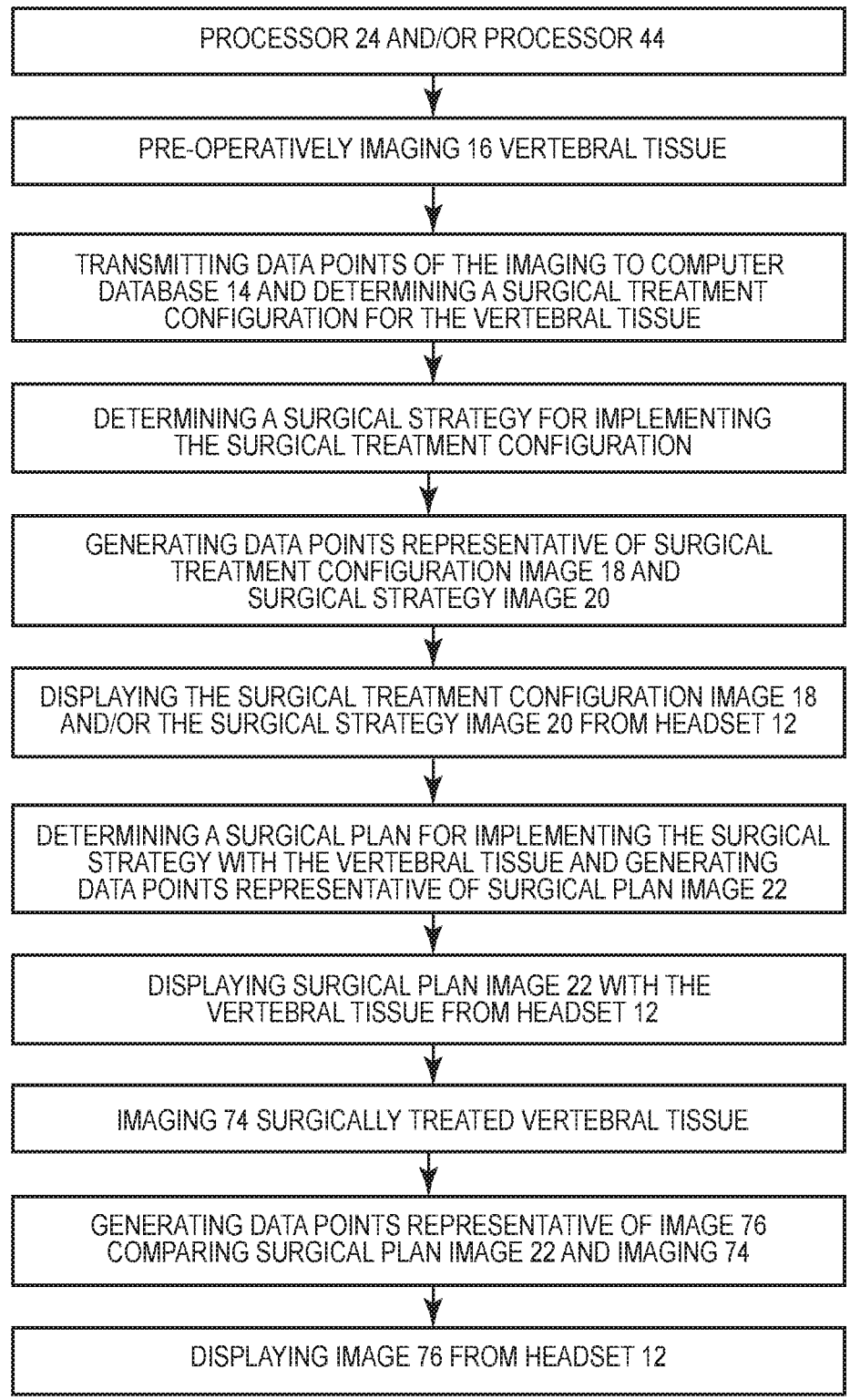
FIG. 5 is a flow diagram illustrating representative steps of one or more embodiments of a method and a surgical system in accordance with the principles of the present disclosure.

Processor 24 and/or processor 44 execute instructions in operation of system 10 for reconciliation of the surgical procedure. As shown in FIG. 5, processor 24 and/or processor 44 execute instructions for pre-operatively imaging 16 vertebral tissue; transmitting data points of the imaging to computer database 14 and determining a surgical treatment configuration for the vertebral tissue; determining a surgical strategy for implementing the surgical treatment configuration; generating data points representative of surgical treatment configuration image 18 and surgical strategy image 20; displaying the surgical treatment configuration image 18 and/or the surgical strategy image 20 from headset 12; determining a surgical plan for implementing the surgical strategy with the vertebral tissue and generating data points representative of surgical plan image 22; displaying surgical plan image 22 with the vertebral tissue from headset 12; imaging 74 surgically treated vertebral tissue; generating data points representative of image 76 comparing surgical plan image 22 and imaging 74 of the surgically treated vertebral tissue; and displaying image 76 from headset 12.

In assembly, operation and use, surgical system 10, similar to the systems and methods described herein, is employed with a surgical procedure, for treatment of a spine of a patient including vertebrae. Surgical system 10 may also be employed with surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 12:
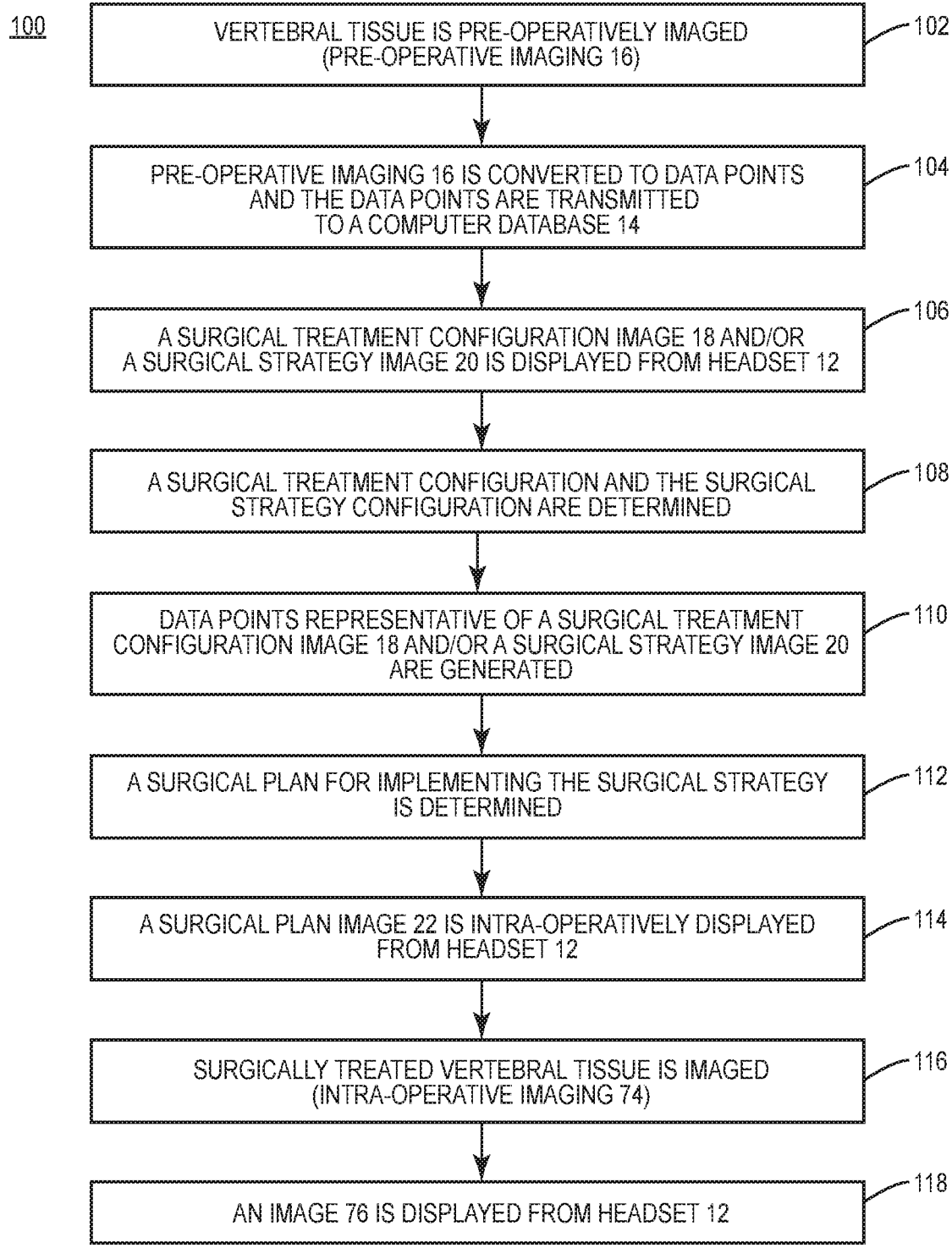
FIG. 12 is a flow diagram illustrating representative steps of one or more embodiments of a method and a surgical system in accordance with the principles of the present disclosure.

In one embodiment, surgical system 10, similar to the components of the systems and methods described herein, is employed in connection with one or more surgical procedures. In some embodiments, system 10 includes a method 100 for surgically treating a spine, as shown in FIG. 12. In a step 102, vertebral tissue of a patient is pre-operatively imaged to generate pre-operative image 16. The vertebral tissue is pre-operatively imaged via an imaging device 36. In some embodiments, imaging device 36 includes a CT scan. In an optional step 104, pre-operative imaging of the vertebral tissue is converted to data points and the data points are transmitted to computer database 14. In some embodiments, the data points are converted by a software program, as described above. Computer database 14 is located on computer 42. In a step 106, an image of a surgical treatment configuration, for example, surgical treatment configuration image 18 for the vertebral tissue is displayed from a mixed reality display and/or an image of a surgical strategy, for example, surgical strategy image 20 for implementing the surgical treatment configuration with the vertebral tissue is displayed from the mixed reality display. The mixed reality display includes headset 12. In some embodiments, the mixed reality display includes a handheld device.

In some embodiments, surgical treatment configuration image 18 includes a segmentation of the vertebral tissue and/or a surgical reconstruction of the vertebral tissue. In some embodiments, surgical strategy image 20 includes a holographic overlay. In some embodiments, surgical strategy image 20 includes a holographic overlay of one or more spinal implants on a surgical reconstruction of the vertebral tissue. In an optional step 108, the surgical treatment configuration for the vertebral tissue and the surgical strategy for implementing the surgical treatment configuration is determined. In some embodiments, surgical treatment configuration image 18 and surgical strategy image 20 are determined and/or generated from a software program, as disclosed above, including, for example, Mazor X™, Mazor X™ Align, and/or Stealthstation™. In an optional step 110, data points representative of the images are generated.

In a step 112, a surgical plan for implementing the surgical strategy is determined. The surgical plan is determined and/or generated from the software described herein. In a step 114, an image of the surgical plan with the vertebral tissue, for example, surgical plan image 22 is intra-operatively displayed from headset 12. In some embodiments, surgical plan image 22 includes a holographic overlay having indicia on the vertebral tissue. In some embodiments, the indicia represent one or more anatomical zones.

In some embodiments, image guidance system 46 and/or robotic guidance system 64, described herein with regard to system 10 are employed with method 100. Data from image guidance system 46 and robotic guidance system 64 is configured for transmission to headset 12. During the surgical procedure, headset 12 is configured to display surgical plan image 22 on the surface of the patient while camera 26 of headset 12 provides real-time images of the patient, as shown in FIGS. 1 and 8. During the surgical procedure, headset 12 displays the storable image of surgical instrument 54 and/or spinal implant 56 and robotic guidance system 64 will assist the surgeon in executing the procedure by operating, delivering and/or introducing surgical instrument 54 and/or spinal implant 56.

In an optional step 116, surgically treated vertebral tissue is imaged, for example, including intra-operative image 74 and/or a post-operative image. Intra-operative image 74 and/or the post-operative image are generated by imaging device 36. In some embodiments, the step of imaging surgically treated vertebral tissue includes an intra-operative CT scan and/or a post-operative CT scan. In an optional step 118, an image 76 comparing surgical plan image 22 and intra-operative image 74 and/or post-operative image is displayed from headset 12. In some embodiments, the step of displaying image 76 includes a holographic reconciliation overlay of the surgical strategy and/or plan to the surgically treated vertebral tissue. Image 76 is determined and/or generated from software described herein.

Figure 13:
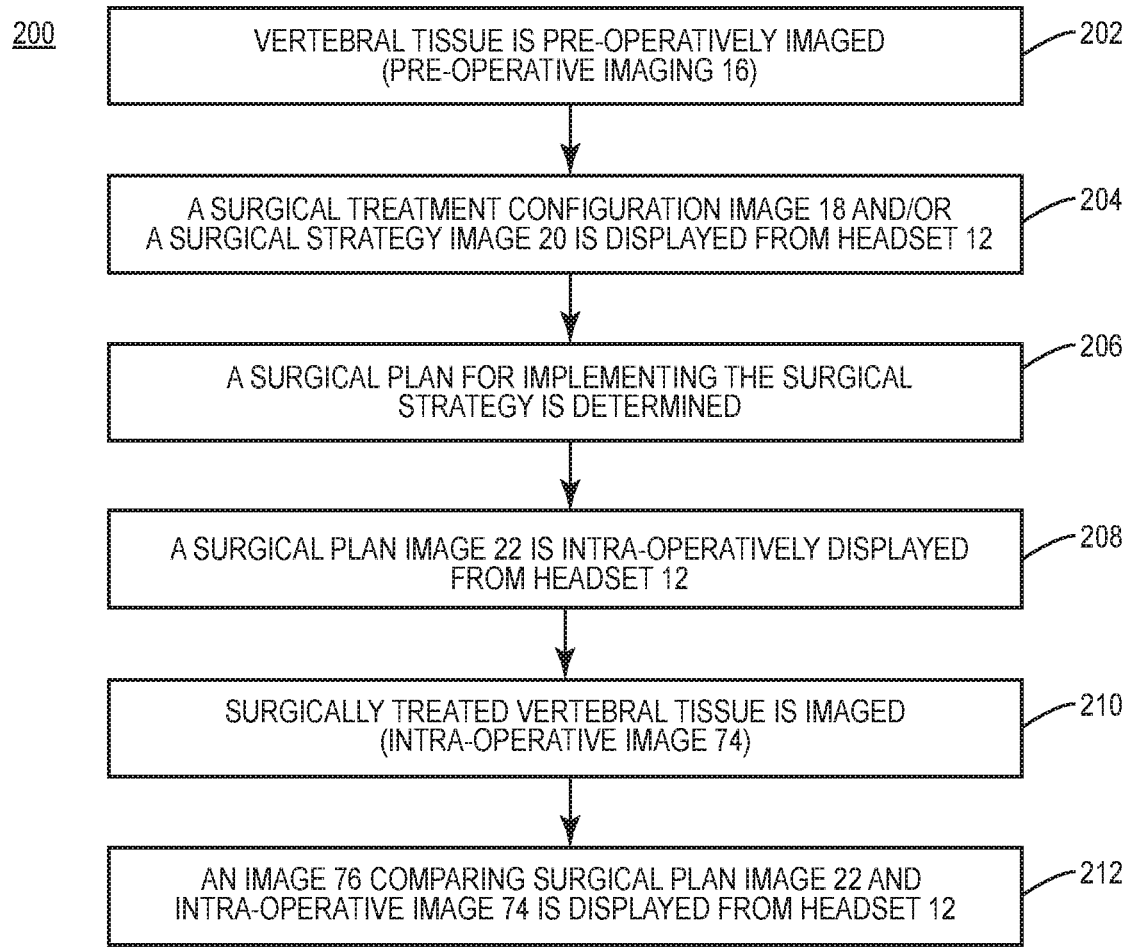
FIG. 13 is a flow diagram illustrating representative steps of one or more embodiments of a method and a surgical system in accordance with the principles of the present disclosure.

In some embodiments, system 10 includes a method 200 for surgically treating a spine, as shown in FIG. 13, similar to method 100, as shown in FIG. 12. In a step 202, vertebral tissue is pre-operatively imaged to generate pre-operative image 16. In a step 204, an image of a segmentation and a surgical reconstruction of the vertebral tissue, for example, surgical treatment configuration image 18 is displayed from a holographic display and/or an image of a surgical strategy that includes one or more spinal implants with the vertebral tissue, for example, surgical strategy image 20 is displayed from headset 12. In a step 206, a surgical plan for implementing the surgical strategy is determined.

In a step 208, an image of the surgical plan with the vertebral tissue, for example, surgical plan image 22 is intra-operatively displayed from headset 12. In an optional step 210, surgically treated vertebral tissue is imaged, for example, including intra-operative image 74 and/or a post-operative image. In an optional step 212, an image 76 comparing surgical plan image 22 and intra-operative image 74 is displayed from the holographic display. In some embodiments, the step of displaying image 76 includes a holographic reconciliation overlay of the surgical strategy and/or surgical plan to the surgically treated vertebral tissue. In some embodiments, surgical plan image 22 includes a holographic overlay having indicia on the vertebral tissue, the indicia representing one or more anatomical zones.

Figure 14:
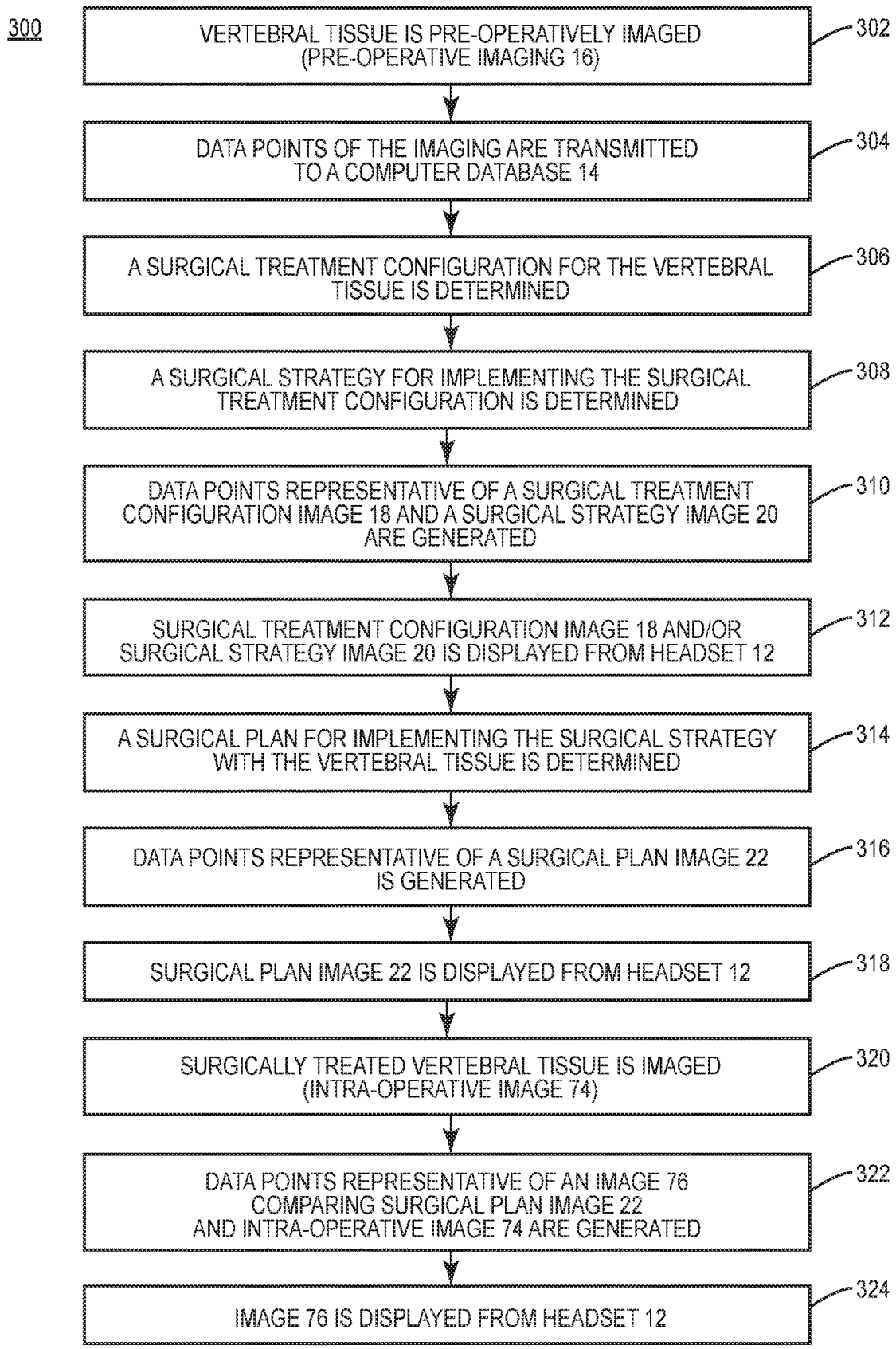
FIG. 14 is a flow diagram illustrating representative steps of one or more embodiments of a method and a surgical system in accordance with the principles of the present disclosure.

In some embodiments, system 10 includes a method 300 for surgically treating a spine, as shown in FIG. 14, similar to method 100, as shown in FIG. 12 and method 200, as shown in FIG. 13. In a step 302, vertebral tissue is pre-operatively imaged to generate pre-operative image 16. In step 304, data points of the imaging are transmitted to a computer database 14. In a step 306, a surgical treatment configuration for the vertebral tissue is determined. In a step 308, a surgical strategy for implementing the surgical treatment configuration is determined. In a step 310, data points representative of an image of the surgical treatment configuration, for example, surgical treatment configuration image 18 and an image of the surgical strategy, for example, surgical strategy image 20 are generated. In a step 312, surgical treatment configuration image 18 and/or surgical strategy image 20 is displayed from headset 12. In a step 314, a surgical plan for implementing the surgical strategy with the vertebral tissue is determined. In a step 316, data points representative of an image of the surgical plan, for example, surgical plan image 22 is generated. In a step 318, surgical plan image 22 is displayed from headset 12.

In a step 320, surgically treated vertebral tissue is imaged, for example, including intra-operative image 74 and/or a post-operative image. In a step 322, data points representative of an image 76 comparing surgical plan image 22 and intra-operative image 74 are generated. In a step 324, image 76 is displayed from headset 12. In some embodiments, the step of displaying image 76 includes a holographic reconciliation overlay of the surgical strategy to the surgically treated vertebral tissue. In some embodiments, surgical plan image 22 includes a holographic overlay having indicia on the vertebral tissue, the indicia representing one or more anatomical zones.

In some embodiments, headset 12 implements software and/or surgical plan image 22 of methods 100, 200 and/or 300 indicates and/or alerts the surgeon, of danger zones located on an anatomy, for example, the vertebral tissue of the patient to assist the surgeon in planning the surgical procedure in the methods described above. In some embodiments, the surgical plan image 22 and/or the software generates a warning to the surgeon if a surgical instrument, for example, a drill or a screw is about to enter into a danger zone or a dangerous area.

In some embodiments, headset 12 implements software and/or surgical plan image 22 enables a surgeon to select specific locations, for example, critical bone faces on anatomical areas of the patient such that an alarm or a warning is generated when the specific locations are in danger of being breached. In some embodiments, headset 12 is configured to auto-recognize the specific locations.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A method for surgically treating a spine, the method comprising the steps of:
   pre-operatively imaging vertebral tissue;
   displaying a first image of a surgical treatment configuration for the vertebral tissue from a mixed reality display and/or a second image of a surgical strategy for implementing the surgical treatment configuration with the vertebral tissue from the mixed reality display;
   determining a surgical plan including robotic guidance for implementing the surgical strategy;
   intra-operatively displaying a third image of the surgical plan with the vertebral tissue from the mixed reality display;
   implementing the surgical plan with the robotic guidance;
   imaging surgically treated vertebral tissue; and
   displaying a fourth image comparing the third image and the imaging of the surgically treated vertebral tissue from the mixed reality display.

2. A method as recited in claim 1, further comprising the steps of transmitting data points of the pre-operative imaging to a computer database; and determining the surgical treatment configuration for the vertebral tissue and the surgical strategy for implementing the surgical treatment configuration.

3. A method as recited in claim 2, further comprising the steps of generating data points representative of the first image and/or the second image.

4. A method as recited in claim 1, wherein the step of imaging surgically treated vertebral tissue includes an intra-operative CT scan.

5. A method as recited in claim 1, wherein the step of displaying the fourth image includes a holographic reconciliation overlay of the surgical strategy to the surgically treated vertebral tissue.

6. A method as recited in claim 1, wherein the pre-operative imaging includes a CT scan.

7. A method as recited in claim 1, wherein the mixed reality display includes a headset.

8. A method as recited in claim 1, wherein the mixed reality display includes a handheld device.

9. A method as recited in claim 1, wherein the second image includes a holographic overlay.

10. A method as recited in claim 1, wherein the surgical treatment configuration includes a segmentation of the vertebral tissue and/or a surgical reconstruction of the vertebral tissue.

11. A method as recited in claim 1, wherein the second image includes a holographic overlay of one or more spinal implants on a surgical reconstruction of the vertebral tissue.

12. A method as recited in claim 1, wherein the third image includes a holographic overlay having indicia on the vertebral tissue, the indicia representing one or more anatomical zones.

13. A method for surgically treating a spine, the method comprising the steps of:
pre-operatively imaging vertebral tissue;
displaying a first image of a segmentation and a surgical reconstruction of the vertebral tissue from a holographic display and/or a second image of a surgical strategy that includes one or more spinal implants with the vertebral tissue from the holographic display;
determining a surgical plan including robotic guidance for implementing the surgical strategy;
intra-operatively displaying a third image of the surgical plan with the vertebral tissue from the holographic display;
implementing the surgical plan with the robotic guidance;
imaging surgically treated vertebral tissue; and
displaying a fourth image comparing the third image and the imaging of the surgically treated vertebral tissue from the holographic display.

14. A method as recited in claim 13, wherein the step of displaying the fourth image includes a holographic reconciliation overlay of the surgical strategy to the surgically treated vertebral tissue.

15. A method as recited in claim 13, wherein the third image includes a holographic overlay having indicia on the vertebral tissue, the indicia representing one or more anatomical zones.

16. A method for surgically treating a spine, the method comprising the steps of:
pre-operatively imaging vertebral tissue;
transmitting data points of the imaging to a computer database and determining a surgical treatment configuration for the vertebral tissue;
determining a surgical strategy for implementing the surgical treatment configuration;
generating data points representative of a first image of the surgical treatment configuration and a second image of the surgical strategy;
displaying the first image and/or the second image from a mixed reality display;
determining a surgical plan including robotic guidance for implementing the surgical strategy with the vertebral tissue and generating data points representative of a third image of the surgical plan;
displaying the third image with the vertebral tissue from the mixed reality display;
implementing the surgical plan with the robotic guidance;
imaging surgically treated vertebral tissue; and
generating data points representative of a fourth image comparing the third image and the imaging of the surgically treated vertebral tissue; and
displaying the fourth image from the mixed reality display, the fourth image including a holographic reconciliation overlay of the surgical strategy to the surgically treated vertebral tissue.

17. A method as recited in claim 16, wherein the third image includes a holographic overlay having indicia on the vertebral tissue, the indicia representing one or more anatomical zones.

* * * * *